United States Patent [19]

Bhatt et al.

[11] Patent Number: 5,994,597
[45] Date of Patent: Nov. 30, 1999

[54] PROCESS FOR RECOVERING HIGH BOILING SOLVENTS FROM A PHOTOLITHOGRAPHIC WASTE STREAM COMPRISING LESS THAN 10 PERCENT BY WEIGHT MONOMERIC UNITS

[75] Inventors: Anilkumar C. Bhatt, Johnson City; Jerome J. Wagner, Endicott, both of N.Y.

[73] Assignee: International Business Machines Corporation, Armonk, N.Y.

[21] Appl. No.: 09/188,006

[22] Filed: Nov. 6, 1998

[51] Int. Cl.$^6$ ............... C07C 29/80; C07C 69/96; C07D 317/36; C07D 307/33
[52] U.S. Cl. ............... 568/810; 549/230; 549/295; 558/260
[58] Field of Search ............... 549/295, 230; 558/260; 568/810

[56] References Cited

U.S. PATENT DOCUMENTS

| | | | |
|---|---|---|---|
| 3,951,769 | 4/1976 | Schlesinger | 204/159.11 |
| 4,187,205 | 2/1980 | Hatano et al. | 260/45.9 D |
| 4,256,774 | 3/1981 | Strobel et al. | 426/428 |
| 4,279,937 | 7/1981 | Strobel et al. | 425/428 |
| 4,413,105 | 11/1983 | Koenig | 525/482 |
| 4,873,174 | 10/1989 | Hsieh et al. | 430/325 |
| 5,066,568 | 11/1991 | Hsieh et al. | 430/325 |
| 5,281,723 | 1/1994 | Bantu et al. | 549/230 |
| 5,296,567 | 3/1994 | Baumann et al. | 526/172 |
| 5,310,428 | 5/1994 | Bhatt et al. | 134/2 |
| 5,411,678 | 5/1995 | Sim | 252/548 |
| 5,427,710 | 6/1995 | Stevens | 252/166 |
| 5,431,739 | 7/1995 | Bengston | 134/2 |
| 5,487,789 | 1/1996 | Sim | 134/38 |

*Primary Examiner*—Ba K. Trinh
*Attorney, Agent, or Firm*—William N. Hogg

[57] ABSTRACT

A method of recovering solvents from an impure effluent stream of an industrial process. The effluent waste stream contains less than about 10 percent by weight of monomeric units that are reacted to form larger oligomers and polymers. The waste stream contains dissolved polymers, polymeric particles, and the hydrolysis, oxidation and/or other decomposition products of one of the solvents. In one embodiment, the first step involves filtering particulate matter from the waste stream. In another embodiment, the filtering step is omitted. The filtered or unfiltered waste stream is fed to a first separation stage for separation into (i) a gaseous stream of water, soluble gases, and volatile contaminants and (ii) a suspension comprising the solvent, water, semi-volatile and non-volatile contaminants, and photoresist products. Following the first separation stage, the dewatered solvent-containing suspension is either distilled or evaporated to separate the solvent from photoresist products and other non-volatile contaminants. Then the solvent-containing suspension is separated into (i) a solvent vapor fraction which contains solvent and semi-volatile contaminants such as plasticizers and monomers, and (ii) a sludge fraction which contains non-volatile contaminants such as polymer and benzoic acid. Thereafter, the solvent vapor fraction is fed into a vapor stripper to strip the semi-volatile contaminants from the solvent vapor fraction using an organic solvent as a mass transfer medium. This removes the semi-volatiles from the solvent-containing vapor fraction and produces a solvent vapor fraction that is essentially pure.

24 Claims, 3 Drawing Sheets

PROCESS FOR RECOVERING HIGH BOILING SOLVENTS FROM A PHOTOLITHOGRAPHIC WASTE STREAM COMPRISING LESS THAN 10 PERCENT BY WEIGHT MONOMERIC UNITS

CROSS-REFERENCE TO RELATED APPLICATIONS

This application is related to application Ser. No. 09/188,007, filed Nov. 6, 1998 (Attorney Docket No. 21325/4024) entitled "Process For Recovering High Boiling Solvents From A Photlithographic Waste Stream Comprising At Least 10 Percent By Weight Of Monomeric Units" filed on the same day as the present application.

BACKGROUND

Photolithography plays a critical role in the art of printed circuit packaging. Photolithography is used to define in a thin film of photoresist those regions from which copper is to be selectively etched to subtractively form circuitization, or to which copper is selectively plated to additively form circuitization. Photolithography is also used to personalize soldermasks and dielectric layers.

There are basically two types of photoresist: negative acting and positive acting. Positive photoresists and negative photoresists are both formed from monomers, hereinafter referred to as "monomeric units", such as, for example, acrylates and ethers of bisphenol A. Examples of monomeric units used in the conventional photoresists are as follows: t-butyl acrylate, 1, 5 pentanediol diacrylate, N,N-diethylaminoethyl acrylate, ethylene glycol diacrylate, 1,4-butanediol diacrylate, diethylene glycol diacrylate, hexamethylene glycol diacrylate, 1,3-propanediol diacrylate, decamethylene glycol diacrylate, decamethylene glycol dimethacrylate, 1,4-cyclohexanediol diacrylate, 2,2-dimethylolpropane diacrylate, glycerol diacrylate, tripropylene glycol diacrylate, glycerol triacrylate, trimethylolpropane triacrylate, pentaerythritol triacrylate, polyoxyethylated trimethylolpropane triacrylate and trimethacrylate and similar compounds as disclosed in U.S. Pat. No. 3,380,831, 2,2-di-(p-hydroxyphenyl)-propane diacrylate, pentaerythritol tetraacrylate, 2,2-di(p-hydrohyphenyl)-propane dimethacrylate, triethylene glycol diacrylate, polyoxyethyl-2,2-di(p-hydroxyphenyl)-propane dimethacrylate, di-(3-methacryloxy-2-hydroxypropyl) ether of bisphenol-A, di-(2-methacryloxyethyl) ether of bisphenol-A, di-(3-acryloxy-2-hydroxypropyl) ether of bisphenol-A, di-(2-acryloxyethyl) ether of bisphenol-A, di-(3-methacryloxy-2-hydroxypropyl) ether of tetrachloro-bisphenol-A, di-(2-methacryloxyethyl) ether oftetrachloro-bisphenol-A,di-(3-methacryloxy-2-hydroxypropyl) etheroftetrabromo-bisphenol-A, di-(2-methacryloxyethyl) ether of tetrabromo-bisphenol-A, di-(3-methacryloxy-2-hydroxypropyl) ether of 1,4-butanediol, di-(3-methacryloxy-2-hydroxypropyl) ether of diphenolic acid, triethylene glycol dimethacrylate, polyoxypropyltrimethylol propane triacrylate, ethylene glycol dimethacrylate, butylene glycol dimethacrylate, 1,3-propanediol dimethacrylate, 1,2,4-butanetriol trimethacrylate, 2,2,4-trimethyl-1,3-pentanediol dimethacrylate, pentaerythritol trimethacrylate, 1-phenyl ethylene-1,2-dimethacrylate, pentaerythritol tetramethacrylate, trimethylol propane trimethacrylate, 1,5-pentanediol dimethacrylate, diallyl fumarate, 1,4-benzenediol dimethacrylate, 1,4-diisopropenyl benzene, and 1,3,5-triisopropenyl benzene.

In addition to the reactive monomeric units mentioned above, the photoimageable compositions used to form negative and positive photoresists can also contain one or more free radical-initiated and polymerizable species with molecular weight of at least about 300. Monomeric units of this type are an alkylene or a polyalkylene glycol diacrylate and those described in U.S. Pat. No. 2,927,022. Particulate thickeners such as, for example, silicas, clays, alumina, bentonites, kalonites, and the like can also be used in the photoimageable compositions. Dyes and pigments may also be added to increase the visibility of the resist image. Any colorant used however, should be transparent to the actinic radiation used to polymerize the monomeric units. With some compositions, it is desirable to add a plasticizer, either solid or liquid, to give flexibility to the film or coating. Generally inert solvents which are volatile at ordinary pressures are used to prepare these photoresist compositions.

During processing of the photoresist, a photoimageable film is first applied to a circuit board and then patterned by exposure of preselected regions to actinic radiation. To develop the resulting pattern of polymerized and unpolymerized material, the coated board is contacted with a liquid developer either by dipping or spraying. The commonly assigned U.S. Pat. No. 5,268,260 of N. R. Bantu, Anilkumar Bhatt, Ashwinkumar Bhatt, G. W. Jones, J. A. Kotylo, R. J. Owen, K. I. Papathomas, and A. K. Vardya for Photoresist Develop and Strip Solvent Compositions and Method for Their Use, incorporated herein by reference, describes the use of the low vapor pressure, high boiling solvents, benzyl alcohol, propylene carbonate, and gamma butyrolactone for developing and stripping acrylate-based photoresist such as DuPont Riston T-168 or photoimageable dielectric material.

In the case of negative acting photoresists, the unpolymerized material used to form the photoresist, i.e., the monomeric units of acrylate or epoxy, is dissolved in the developer at low temperature, preferably between 15° C. and 45° C. The dissolved material, which consists primarily of monomeric units of the acrylate or epoxy, and the developing solution are then removed from the board by allowing the solution to run off into a containment tank. To further enhance development of the pattern, the residual dissolved material and developing solution are rinsed from the board, preferably with warm water. High vapor pressure organic solvents, such as isopropyl alcohol, acetone, methyl ethyl ketone and xylene, may also be used as a rinse. Positive acting resists behave oppositely. Actinic radiation renders the positive acting photoresist more soluble in the developer, and the exposed regions are removed preferentially by the developer. The effluent produced by this process is an impure solution of developer, which is laden with monomeric units and other impurities. Typically, the effluent of such process contains greater than 10 percent weight of monomeric units.

Following circuitization of the board, the polymerized photoresist may be stripped from the board, preferably by spraying with a stripping solution at elevated temperatures, preferably between 50° C. and 100° C. The commonly assigned U.S. Pat. No. 5,268,260 of Bantu et al also describes the use of benzyl alcohol, propylene carbonate, and gamma butyrolactone for stripping acrylate-based photoresist such as DuPont Riston T-168. The stripping solution causes the polymerized photoresist to swell, and debond, i.e., detach from the underlying substrate, and flake off of the board. The stripping can be assisted by gentle scrubbing with brushes. The resist particles and stripping solution are then removed from the board, preferably by flushing into a containment tank. Any residual polymerized film particles and stripping solution are rinsed from the package, preferably at elevated pressures, preferably with warm water. The water rinse can be replaced by rinsing in high vapor pressure solvents. The effluent produced by this process is an impure solution of stripper, laden with dissolved polymeric photoresist, suspended particles of polymeric photoresist and other impurities. Typically, such effluent contains less than 10 percent by weight monomeric units, and possibly as little as zero weight percent monomeric units.

Large volumes of liquid waste containing an impure low vapor pressure, high boiling solvent result from the above-described processes. This liquid waste must be further processed prior to release into the environment, as by incineration. Such methods of dealing with the liquid waste are costly. Moreover, the costs to the industry in terms of purchasing virgin material, i.e., pure benzyl alcohol, pure gamma butyrolactone, and pure propylene carbonate, and the costs to the environment of manufacturing virgin material are significant.

Accordingly, it is desirable to have a new method of reducing the amount of liquid waste that results from these and other industrial processes. A method that permits recovery of relatively pure benzyl alcohol, propylene carbonate, or gamma butyrolactone which can then be re-used by the industry, and thus prevent the need to purchase virgin material, is especially desirable.

SUMMARY OF THE INVENTION

In accordance with the present invention, a method of recovering benzyl alcohol, gamma butyrolactone, or propylene carbonate from an impure effluent stream of an industrial process is provided. The effluent waste stream contains less than about 10 percent by weight of monomeric units that are reacted to form larger oligomers and polymers. Typically, the waste stream contains dissolved polymers, polymeric particles, and the hydrolysis, oxidation and/or other decomposition products of one of the high boiling solvents. Thus, an effluent stream which contains benzyl alcohol, typically, will also contain benzoic acid and/or benzaldehyde. An industrial processing effluent stream which contains gamma butyrolactone, typically, will contain gamma butyric acid and/or hydroxybutyric acid. An industrial processing effluent stream which contains propylene carbonate, typically, will also contain propylene glycol, propylene oxide and carbon dioxide. Such waste streams are produced when benzyl alcohol, propylene carbonate, or gamma butyrolactone is used as a stripper in a photolithographic process.

In one embodiment, the first step in the method involves filtering particulate matter, especially particles of the processed photoresist, from the waste stream. In another embodiment, the filtering step is omitted. The filtered or unfiltered waste stream is fed to a first separation stage where the waste stream is separated into (i) a gaseous stream of water, soluble gases, and volatile contaminants and (ii) a suspension comprising the high boiling solvent, water, semi-volatile and non-volatile contaminants, and photoresist products. The term "photoresist products" is used hereinafter to describe dissolved monomer, suspended polymers of the processed photoresist and any remaining particles of the processed photoresist that have not been removed by filtering. The first separation stage lowers the concentration of water in the suspension to a level that is low enough to substantially avoid further hydrolysis of the solvent in subsequent steps of the method.

Following the first separation stage, the dewatered solvent-containing suspension is either distilled or evaporated to separate the solvent from high boiling photoresist products and other non-volatile contaminants. In this stage the solvent-containing suspension is separated into (i) a solvent vapor fraction which contains solvent and semi-volatile contaminants such as plasticizers and monomers, and (ii) a sludge fraction which contains non-volatile contaminants such as polymer and benzoic acid.

Thereafter, the solvent vapor fraction is fed into a vapor stripper where the semi-volatile contaminants are stripped from the solvent vapor fraction using an organic solvent as a mass transfer medium. This step removes the semi-volatiles from the solvent-containing vapor fraction and produces a solvent vapor fraction that is essentially pure.

DETAILED DESCRIPTION OF THE INVENTION

Industrial processes which employ relatively pure benzyl alcohol, propylene carbonate or gamma butyrolactone as a stripper to remove polymerized photoresist products from a printed circuit board result in the production of an impure benzyl alcohol effluent, an impure propylene carbonate effluent, or an impure gamma butyrolactone effluent, respectively. Such effluents typically contain (i) above about 50 weight percent solvent, and generally from about 85 weight percent to about 97 weight percent solvent, (ii) up to about 30 weight percent photoresist products and other solids, and generally from about 1 weight percent to about 25 weight percent of the photoresist products and other solids, (iii) up to about 5 weight percent, and generally from about 0.05 weight percent to about 1 weight percent decomposition products of the respective solvent, and (iv) up to about 20 weight percent, and generally from about 0.05 weight percent to about 5 weight percent of water. These weight percentages should total 100 weight percent but may total less than 100 weight percent if other impurities are present. For example, the effluent may be a combination of effluents from the developing steps and the stripping steps of a photolithographic process. In such case, the effluent, typically, comprises monomeric units at a concentration of less than 10 percent by weight of the effluent, as well as surfactants, initiators, initiator fragments, fillers, and dyes, which collectively are referred to herein as "materials".

While the invention is described and illustrated with respect to recovery of benzyl alcohol, gamma butyrolactone, and propylene carbonate, it is, of course, to be understood that the method can also be applied to other aromatic alcohols, such as for example 1- benzyl benzyl alcohol, benzyl tertiary butanol, 2 benzyloxy ethanol, 5-phenyl-1 pentanol, phenyl ethyl alcohol, 3-(n-benzyl-n-methyl amino)-1-propanol. The optimum temperatures and pressures for recovery of these aromatic alcohols via the present method are easily determined and within the ordinary skill of the art.

In order to recycle the low vapor pressure, high boiling solvent for reuse as a developing agent or stripping agent, it is necessary to recover a purified solvent. By purified solvent is generally meant a solvent that is typically 99 or greater weight percent pure; that is essentially free of monomeric units and materials; and that contains less than about 0.1 weight percent water, and preferably less than about 0.05 weight percent water, and less than 0.01 weight percent of the decomposition products of the solvent, as assayed by gas chromatography.

Figure 1:
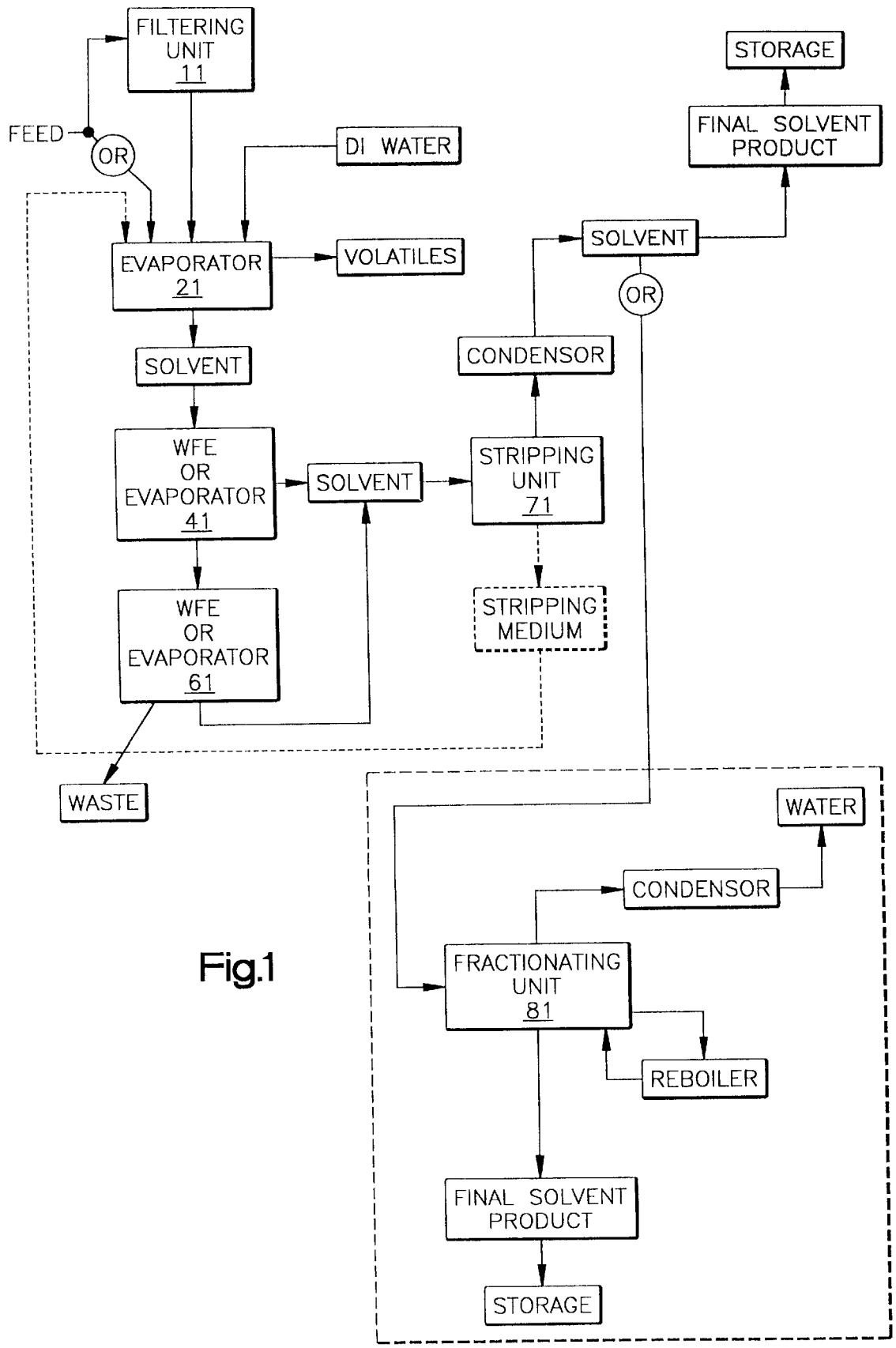
FIG. 1 is a flow chart which generally exemplifies a process for recovering a low vapor pressure, high boiling solvent from a waste stream comprising less than about 10 weight percent of monomeric units, such as acrylates.

FIG. 1 is a flow chart which exemplifies a process for recovering a low vapor pressure, high boiling solvent, such as benzyl alcohol, from an effluent stream of a process in which such solvent is used as a photoresist stripper. In one embodiment of the recovery process illustrated in FIG. 1, the effluent stream is initially fed to dewatering unit 21. In another embodiment, the effluent stream is fed to a filtering unit 11 prior to feeding to the dewatering unit 21.

Figure 2:
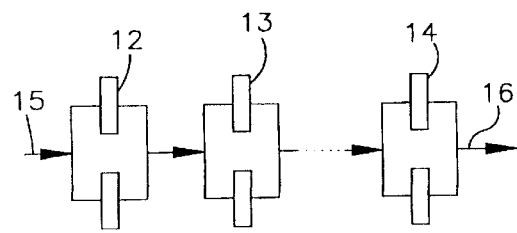
FIG. 2 is a schematic representation of a filtration unit for removing polymeric particles of processed photoresist from the effluent waste stream.

Filtering unit 11 filters particulate matter, primarily particles of cross-linked photoresist, from the effluent waste stream. In the dewatering unit, the effluent stream is separated into two streams: (i) a gaseous stream of water and volatiles and (ii) a liquid stream which contains the high boiling solvent. The dewatering unit may be a short tube, vertical pipe heat exchanger type evaporator 21, as shown in FIG. 2. Alternatively, the first stage separator may be a boiling pot, flash evaporator, or any other type of heater which allows for removal of the water-bearing vapor stream from the liquid solvent-containing stream.

This first separation stage lowers the concentration of water in the liquid stream to a level that is low enough to substantially avoid hydrolysis of the low vapor pressure, high boiling solvent to the corresponding decomposition product. In the first stage separator, as heat exchanger type evaporator 21, the total pressure is maintained higher than the vapor pressure of the solvent at its open cup flash point. The temperature of the process stream is maintained at a temperature below the flash cup point of the solvent. Accordingly, in the first stage separator, the effluent stream which comprises benzyl alcohol is maintained at a temperature of from about 80° C. to about 90° C., and the total pressure in evaporator 21 is maintained at corresponding levels of from about 15 torr to about 25 torr. When the effluent stream comprises gamma butyrolactone, the temperature of the waste stream is maintained at about 75° C. to about 85° C. and the total pressure in evaporator 21 is maintained at corresponding levels of about 20 torr to about 35 torr. When the effluent stream comprises propylene carbonate, the temperature of the waste stream is maintained at about 115° C. to about 125° C. and the total pressure in evaporator 21 is maintained at corresponding levels of about 25 torr to about 35 torr.

The bottom product of the first separation stage is a dewatered solvent, preferably containing (i) from about 90 weight percent to about 98 weight percent of the respective solvent, (ii) from about 1 weight percent to about 25 weight percent of materials, photoresist products and other solids, (iii) from about 0.03 weight percent to about 1 weight percent of the decomposition product of the solvent, and (iv) from about 0.03 weight percent to about 0.1 weight percent of water.

The dewatered solvent from the first stage separation is then distilled or evaporated, preferably in a wiped film type evaporator 41, to separate the solvent from non-volatile contaminants. When the dewatered solvent comprises benzyl alcohol, the pressure in the evaporator 41 is maintained below about 15 torr, for example from about 5 to about 11 torr and the temperature is maintained at corresponding values of from about 81° C. to about 95° C. When the dewatered solvent comprises propylene carbonate, the pressure in evaporator 41 is maintained below about 30 torr, for example from about 6 torr to about 22 torr and the temperature is maintained at a corresponding value of from about 116° C. to about 127° C. When the dewatered solvent comprises gamma butyrolactone, the pressure in evaporator 41 is maintained below about 25 torr, for example from about 8 torr to about 20 torr and the temperature is maintained at a corresponding value of from about 76° C. to about 93° C. In this stage dewatered solvent is separated into a solvent-containing vapor fraction, and a sludge fraction. The sludge fraction, i.e., the bottom product, contains inert contaminants, such as fillers, and non-volatile contaminants, such as benzoic acid, in the corresponding solvent. The solvent-containing vapor fraction from this second stage separation, i.e., overhead product, is from about 95 to about 99 weight percent solvent.

Figures 5, 6:
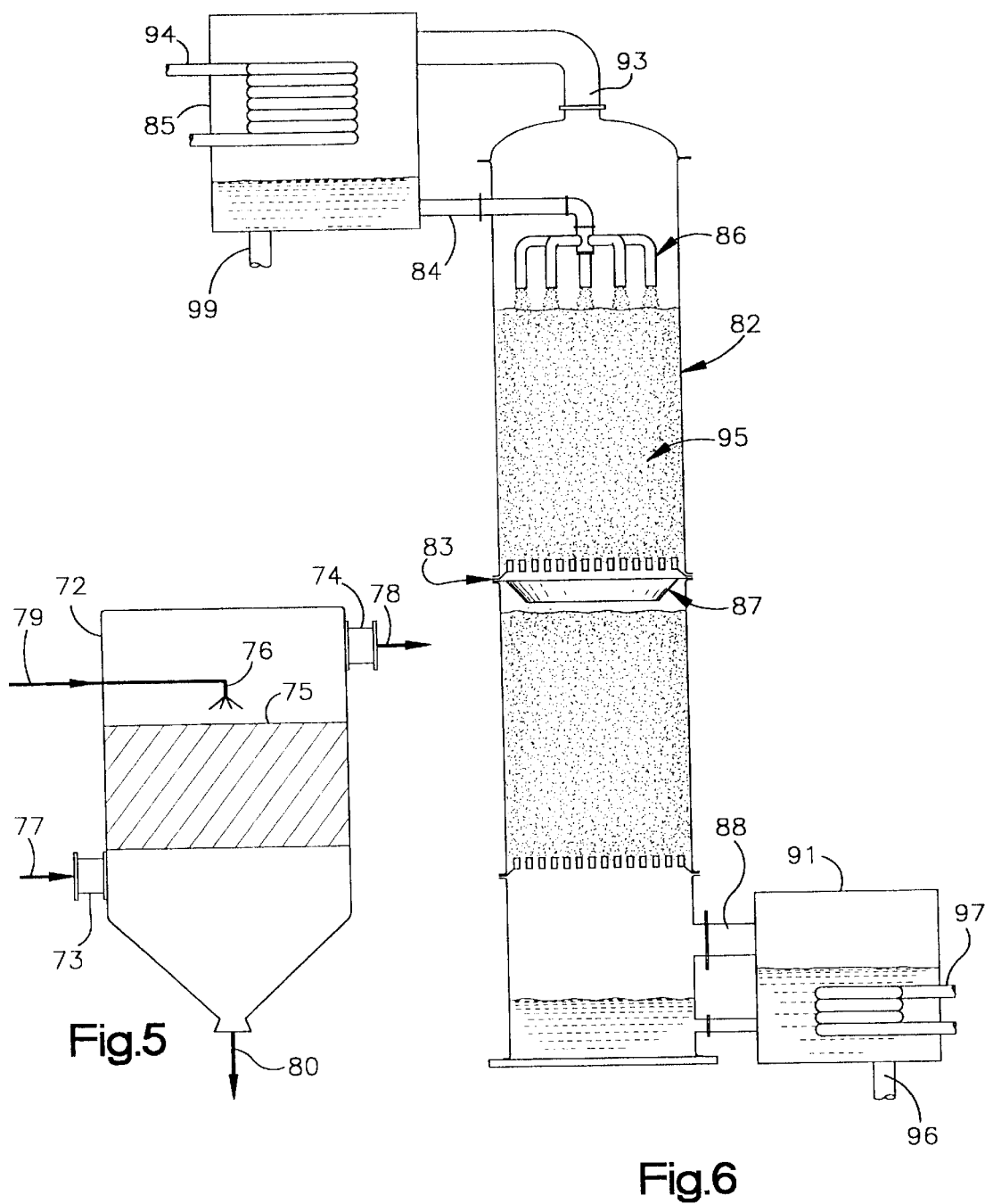
FIG. 5 is a schematic representation of a stripping unit useful in separation of the solvent from semi-volatile materials.
FIG. 6 is a cutaway view of a packed tower distillation column useful in separation of the solvent from higher vapor pressure, lower boiling contaminants.

The overhead product, i.e., the dewatered, evaporated solvent-containing vapor fraction is fed to stripping unit 71, which may be a packed mass transfer unit, as shown in FIG. 5. In stripping unit 71, semi-volatile contaminants, such as plasticizers and any remaining monomeric units, are removed from the vapor using a cool, compatible, liquid solvent, as a mass transfer medium. As used herein, "cool" means that the temperature of the mass transfer medium is at least about 20° C. less than the temperature of the vapor. Preferably, the temperature of the mass transfer medium is between about 35° C. to about 70° C. Preferably, the ratio of the mass transfer medium to vapor mass is about 1:7.

In stripping unit 71, heat from the vaporized semi-volatile contaminants is transferred to the mass transfer medium. Such transfer causes the semi-volatile contaminants to condense to liquid, which results in their removal from the vapor stream. Concurrently, a small amount of the mass transfer medium is vaporized and enters the product stream. Accordingly, to avoid introduction of other contaminants into the vapor fraction, it is preferred that a relatively pure benzyl alcohol be used as the mass transfer medium when benzyl alcohol is the primary solvent in the waste stream.

The top product of this stage is a solvent-containing vapor which is subsequently condensed into a stripped solvent fraction containing greater than about 96 weight percent solvent. The bottom product is a liquid containing the mass transfer medium and the semi-volatile species. In those cases where the mass transfer medium employed is the same as the solvent being recovered, it is preferred that the bottom product be fed back to the first stage evaporator 21 to increase recovery of the respective solvent.

Depending upon purity requirements, the stripped solvent fraction may either be stored for future use or further purified. Further purification is accomplished by feeding the stripped solvent-containing fraction to a fractionating unit 81, which may be a packed tower of the type shown in FIG. 6. In fractionating unit 81, the stripped solvent containing fraction is separated into a higher vapor pressure, lower boiling point top product (fractionation waste) and a lower vapor pressure, higher boiling bottom product, hereinafter referred to as the "final solvent product". Preferably a reboiler heats fluid which is collected from and recycled back into the bottom of fractionating unit 81. A cool condensate is introduced into the top of fractionating unit 81.

In those instances where the stripped solvent containing fraction comprises benzyl alcohol, it is preferred that the top pressure of fractionating unit 81 be less than about 10 torr, and generally from about 1 to about 4 torr, and the bottom pressure be less than about 25 torr, and generally from about 10 to about 20 torr. The top product of such process is benzaldehyde and the bottom product is benzyl alcohol that is about 99 or greater weight percent pure. In those instances where the stripped solvent containing fraction comprises propylene carbonate, it is preferred that the top pressure of the fractionating unit be less than about 15 torr, and generally from about 4 torr to about 10 torr, and the bottom pressure be less than about 25 torr, and generally from about 15 to about 20 torr. The top product of such process is water and propylene glycol and the bottom product is propylene carbonate that is about 99 or greater weight percent pure. In those instances where the stripped solvent containing fraction comprises gamma butyrolactone, it is preferred that the top pressure of the fractionating unit be less than about 10 torr, and generally from about 2 torr to about 5 torr, and the bottom pressure be less than about 25 torr, and generally is from about 15 torr to about 20 torr. The top product of such process is water and hydroxybutyric acid and/or gamma butyrolactone and the bottom product is gamma butyrolactone that is about 99 or greater weight percent pure.

The product of fractionating unit 81, i.e., the final solvent product, is about 99 or greater weight percent solvent and is essentially free of materials, photoresist products, and other solids. The final solvent product is also essentially free of water and decomposition products of the solvent, containing less than about 0.03 weight percent water and less than about 0.01 weight percent of the decomposition products.

Optionally, the low vapor pressure, high boiling solvent may also be recovered from the bottom product of evaporator 41, i.e., from the sludge fraction. The bottom product contains inert contaminants, such as fillers, and non-volatile contaminants, such as benzoic acid, in the corresponding solvent. The bottom product contains from about 70 to about 95 weight percent solvent, balance solids. In this optional step, the bottom product of the evaporator 41 is fed to a further evaporator 61. The overhead product of the second evaporator goes to stripping unit 71 as shown in FIG. 1. The bottom product of the evaporator unit 61 is a polymer rich material that is discharged and collected in storage tanks or drums. If the collected waste product contains greater than about 20 weight percent reactive monomer, it is preferred that from about 5 ppm to about 500 ppm of an antioxidant or stabilizer be added to the collected waste product. Exemplary stabilizers are quinone type stabilizers, such as hydroquinone, p-methoxy phenol, alkyl substituted hydroquinones, aryl substituted quinones, tert-butyl catechol, pyrogallol, naphthylamines, beta-napthol, 2,6-di-tert-butyl-p-cresol, phenothiazine, pyridine, nitrobenzene, dinitrobenzene, p-toluene quinone, hydroquinone monomethyl ether, as well as copper organo-metallics.

Optionally, to reduce combustion potential, all process steps are conducted under a nitrogen blanket. The use of a nitrogen blanket also provides a higher quality product. Alternatively, from about 5 ppm to about 500 ppm of stabilizer is added to the waste stream prior to processing in evaporators 21 and/or 41, and/or prior to waste shipment. Addition of the stabilizer prevents exothermic reactions from occurring during the various processing steps and shipment. Accordingly, addition of such stabilizer is especially desirable when the respective waste stream or waste product contains greater than about 20 weight percent reactive monomer.

Turning now to the individual process steps, the first step in one embodiment of the process involves filtration of particulate matter such as for example particles of cross-linked photoresist from the waste stream. This is shown in FIG. 2 as being carried out by passing the effluent waste stream 15 through a series of filter banks. Filter banks 12, 13, and 14 contain one or more parallel filter elements for removing particulate matter from waste stream 15. The pore sizes of the filter elements are selected to satisfy particular process and economic requirements. Generally, lead filter bank 12 is sized to remove large particles. For example, lead filter bank may be sized to remove particles of a size equal to or greater than 200 microns. Subsequent filter banks 13 and 14 hold filter elements sized to capture successively smaller particles. Generally, the pores in the final filter element in filter bank 14 are from about 5 microns to about 20 microns in diameter to ensure that filtered effluent stream 16 is essentially free of solid particulate matter.

Figure 3:
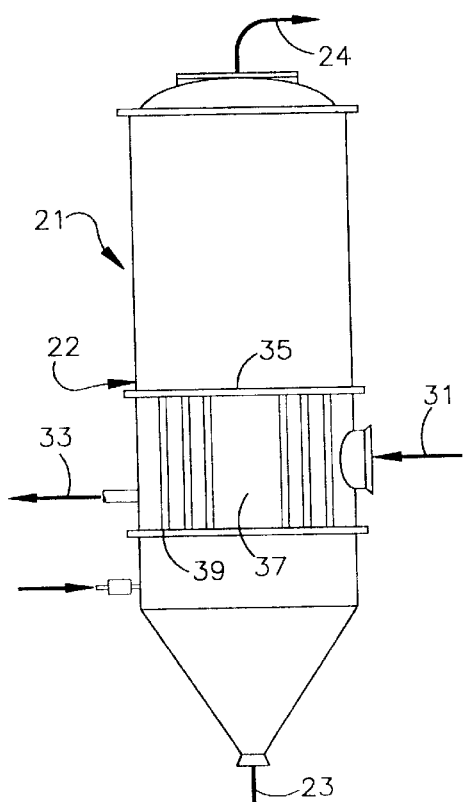
FIG. 3 is a cutaway view of single stage, vertical tube heat exchanger type evaporator useful in separating the solvent from water and volatiles.

Thereafter, the effluent is fed to a dewatering unit 21, which is shown in FIG. 3 as being a short tube vertical heat exchanger type evaporator 21, such as a falling film type evaporator. In another embodiment, the effluent waste stream is not filtered prior to being fed to the dewatering unit 21.

The short tube vertical heat exchanger type evaporator 21 has a feed stream 22, which is separated in the evaporator 21 into a bottom or liquid stream 23 and an overhead or gas stream 24. Additionally, water, for example, deionized water, may be fed to the top of the evaporator. Heat transferred to this water from the gas stream aids in condensing the solvent vapor, i.e., the benzyl alcohol, gamma butyrolactone, or propylene carbonate in the gas stream, and thereby reduces the loss of the desired solvent with the overhead 24.

Steam enters the heat exchanger type evaporator 21 through steam inlet 31, which is the inlet to a shell and tube type heat exchanger 21. The steam is the shell side medium. In one exemplification the tubes 39 are vapor risers. Evaporating feed rises through the tubes or vapor risers 39. Steam condensate exits the shell and tube heat exchanger 31 through outlet 33.

The total pressure in vertical heat exchanger type evaporator 21 is maintained higher than the vapor pressure of the solvent at its open cup flash point. The temperature of feed stream 22 is raised to a temperature which is approximately 2 to 10° C. below the open flash cup point of the solvent, thereby flashing water and other volatile species and gases from the liquid stream. Accordingly, in the first stage separator, the effluent stream which comprises benzyl alcohol is maintained at a temperature of from about 80° C. to about 90° C., and the total pressure is maintained at from about 15 to about 25 torr. When the effluent stream comprises gamma butyrolactone, the temperature of the waste stream is maintained at about 75° C. to about 85° C. and the total pressure in evaporator 21 is maintained at about 20 torr to about 30 torr. When the effluent stream comprises propylene carbonate, the temperature of the waste stream is maintained at about 115° C. to about 125° C. and the total pressure in evaporator 21 is maintained at about 25 torr to about 35 torr.

Figure 4:
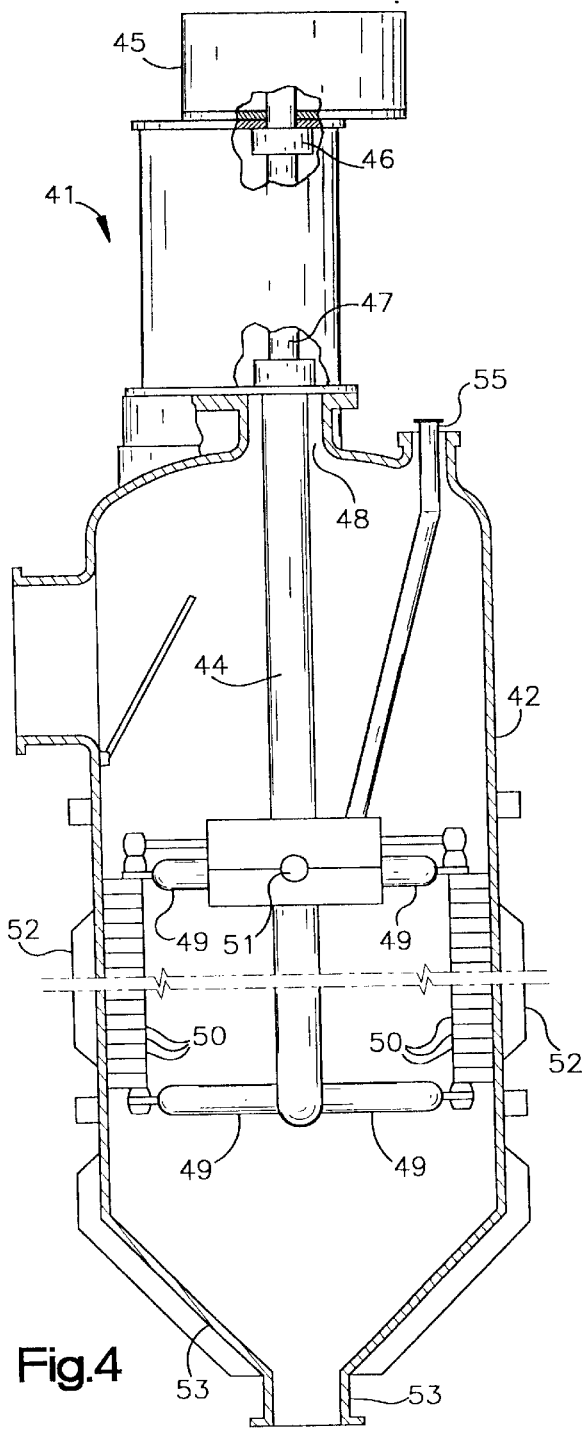
FIG. 4 is a cutaway view of a wiped film evaporator useful in separation of the solvent from non-volatile materials and contaminants.

The liquid product 23 of the first stage separation 21 is then fed to the second stage separation 41. The second stage separator 41 is illustrated in FIG. 4 as a single-effect wiped film evaporator.

A wiped film evaporator 41 has a cylindrical vessel, 42, as a steel vessel. The interior walls of the vessel may be metal, as stainless steel, super alloys, and the like. Alternatively, the interior walls may be lined, for example, with glass or an enamel. By an enamel is meant a porcelain enamel. Porcelain enamels are vitreous or partially devitrified inorganic materials. The glass or enamel lining is bonded to the steel vessel 42.

Wiped film evaporators 41 are characterized by a rotating wiper assembly 43 extending along the vertical axis of the evaporator 41. The rotating wiper assembly 43 includes a rotating shaft 44, arms 49 extending outwardly from the rotating shaft 44, and blades 50 at the ends of the arms 49 for spreading the solvent solution onto the interior wall of the vessel 42.

The rotating shaft 44 is driven by a motor 45, through bearings 46, and coupling 47, extending through a seal 48 in the top of the vessel. The walls of the wiped film evaporator 41 are heated by seam in steam jackets 52.

In operation, the dewatered solvent of the first stage evaporator 21 is introduced into the wiped film evaporator 41 through opening 55. The liquid feed is led to a distributor 51. Centrifugal force and gravity drive the solvent out of the distributor 51 to the blades 50 at the ends of the arms 49. The blades 50 spread the solvent onto the interior surface of the vessel 42, where the steam in the steam jacket 52 heats the solvent giving off a solvent vapor 57. The liquid residues fall to a conical collecting region 53 and outlet 54.

The liquid product of the second stage separation 41 may be further processed, for example through use of a downstream evaporator 61, to concentrate the resist solids and increase solvent distillate yield. The final residue of the downstream evaporator 61 becomes a principal waste of the process.

Vapors from units 41 and 61, being solvent substantially free of photoresist materials but containing minor amounts of other volatiles and semi-volatiles such as plasticizers and monomeric units, are fed to a stripping unit 71 where components that are less volatile than the solvent are transferred to a mass transfer medium. The temperature of mass transfer medium is at least about 20° C. lower than temperature of vapor and, preferably, from about 35° C. to about 70° C. The operating pressure within stripping unit 71 varies from a lower pressure at the top where the stripped solvent vapor exits stripping unit 71 to a slightly higher pressure at the bottom where the vapor stream from evaporator 41 enters stripping unit 71.

When the solvent is benzyl alcohol, the pressure in the vapor inlet of the stripping unit is maintained below about 15 torr, for example from about 5 to about 11 torr. When the solvent is propylene carbonate, the pressure in the vapor inlet of the stripping unit is maintained below about 30 torr, for example from about 12 torr to about 22 torr. When the solvent is gamma butyrolactone, the pressure in the vapor inlet of the stripping unit is maintained below about 25 torr, for example from about 8 torr to about 20 torr.

Vapors 77 from units 41 and 61 enter the vapor stripper unit 71 through the vapor inlet connection 73 which, typically, is positioned near the bottom of the equipment shell 72. The vapor flows upward through mass transfer contact means 75, which may be of random packing style, structured packing style, bubble tray style, or any other style which permits contacting of vapor with the liquid stripping medium. While flowing through mass transfer contact means 75, the vapor stream is contacted with downward-flowing, cool, clean liquid mass transfer medium 79, which has been distributed over contact means 75 by liquid distributor 76. While flowing through contact means 75, the vapor is stripped of semi-volatile components. Stripped vapor 78 exits the shell of equipment through vapor outlet 74, which, typically, is located near the top of shell 72. The exiting liquid stripping stream 80, which now contains semi-volatile species, leaves shell 72 from the bottom of the unit. Movement of the vapor in vapor stripper 71 is caused by pressure differences in the equipment as shown in FIG. 1, with the vapor moving from the higher pressure evaporators 21 and 41 towards the lower pressure condenser. Movement of the liquid stripping media in the vapor stripper 71 is caused by gravity.

Mass transfer medium 79 must be compatible liquid which is non-reactive with the vapor chemistry. Mass transfer medium 79 is selected such that the semi-volatile species are soluble in mass transfer medium 79 at the concentrations and under the conditions which exist in vapor stripping unit 71 during processing of the vapor stream.

Solvent vapors from stripping unit 71 are then condensed into a stripped liquid solvent product that may be stored for future use. Optionally, a portion of the stripped liquid solvent is recycled back to stripping unit 71 for use as mass transfer medium 79.

If desired, the stripped liquid solvent product is introduced into a fractionation column 81 for further purification. In the fractionation column 81, components that are more volatile than the solvent form a vapor phase which is removed from the top of the column and then condensed. The components in the vapor phase include water and decomposition products of the solvent which is being recovered. Examples of decomposition products of the high boiling solvents are benzaldehyde, hydroxybutyric acid and/or gamma butyric acid, propylene glycol, and propylene oxide.

Fractionation occurs within this unit, with more volatile species traveling to the top of column 81 to be condensed and the less volatile solvent circulating within the bottom of the column 81 as a liquid cooler than its boiling point. Normal methods of distillation column operation, including control of overhead reflux ratio and of bottom reboil ratio, are applied. Condensation is effected by a reflux stream introduced at the top of the column 81. A liquid stream comprising solvent leaves the bottom of column 81. This stream may be removed from the system and stored as the final solvent product. Alternatively, the liquid stream may be introduced into a re-boiler, which heats the liquid and revaporizes more volatile contaminants. The vapor product from the reboiler is re-introduced into the fractionation column for further purification.

In instances where the stripped solvent is benzyl alcohol, the operating pressure within the column 81 varies from about 1 to about 4 Torr at the top to about 10 to about 20 Torr at the bottom. In instances where the stripped solvent is gamma butyrolactone, the operating pressure within the column 81 varies from about 2 to about 5 Torr at the top to about 15 to about 20 Torr at the bottom. In instances where the stripped solvent is propylene carbonate, the operating pressure within the column 81 varies from about 4 to about 10 Torr at the top to about 15 to about 20 Torr at the bottom.

Details of a packed tower distillation column 81 are shown in FIG. 6. Structurally, the packed tower 81 includes a shell or body 82, with a condenser 85 at the top and a reboiler 91 at the bottom. Feed is introduced into the tower 81 through liquid feed means 83, to a liquid distributor similar to 86, and a packing restrainer 87 (the feed location may be at about one-half of the tower's height.) The liquid distributor 86 and the packing restrainer 87 distribute the feed and the condenser return 84 onto and through the packing 95.

Upward flowing gas, for example, return 88 from the reboiler 91, contacts the downward flowing liquid, providing a low boiling, high vapor pressure top product 93 at the condenser 85, which is condensed by a condenser heat exchanger 94 and recovered as a high vapor pressure, low boiling temperature liquid 99, and a high boiling, low vapor pressure product at the reboiler 91, which is recovered as a liquid product 96. The remaining reboiler liquid is vaporized by heat exchanger 97. A final solvent product, suitable for re-use in manufacturing, is discharged from the bottom of the fractionation column 81 or from liquid product 96.

While the invention has been described with respect to certain preferred embodiments and exemplifications, the invention may also be used to purify solvents from other industrial processes. Accordingly, the methods described herein may also be used to purify the low vapor pressure, high boiling solvents from waste streams comprising ionic materials and contaminants, color bodies, polymers, oils, paints, carbon, and resins as well as photoresist products. It is not intended to limit the scope of the invention to the preferred embodiments and exemplifications, but solely by the claims appended hereto.

What is claimed is:

1. A method of recovering an organic solvent from an effluent stream comprising said solvent, water, and less than about 10 weight percent of monomeric units, said method comprising the steps:
   (a) feeding the effluent stream into a first stage separator and separating water and volatiles from the effluent stream to provide a dewatered solvent fraction;
   (b) feeding the dewatered solvent fraction into a second stage separator to separate the dewatered solvent from high boiling and nonvolatile materials, and recovering therefrom a vapor fraction containing said solvent; and
   (c) stripping semi-volatile species from said vapor fraciton to provide a stripped liquid solvent.

2. The method of claim 1 wherein the solvent is selected from the group consisting of benzyl alcohol, gamma butyrolactone, and propylene carbonate.

3. The method of claim 1 further comprising the step of filtering said effluent stream to remove particles therefrom prior to step (a).

4. The method of claim 1 further comprising the step of separating the stripped liquid solvent into a higher vapor pressure fraction comprising substances more volatile than said solvent and a lower vapor pressure fraction comprising said solvent.

5. The method of claim 3 further comprising the step of separating the stripped vapor fraction into a higher vapor pressure fraction comprising substances more volatile than said solvent and a lower vapor pressure fraction comprising said solvent.

6. The method of claim 1 wherein the temperature is maintained below the open cup flash point of the solvent.

7. The method of claim 1 wherein said solvent is benzyl alcohol and the pressure in said first stage separator is maintained below about 25 torr.

8. The method of claim 1 wherein the solvent is an aromatic alcohol.

9. The method of claim 1 wherein the first stage separator is a heat exchanger type evaporator.

10. The method of claim 1 wherein the second stage separator is a wiped film evaporator.

11. The method of claim 1 wherein one or more of steps (a), (b), and (c) are performed under a nitrogen blanket.

12. The method of claim 1 wherein from about 5 ppm to about 500 ppm of a stabilizer is added to the effluent waste stream prior to step (a).

13. The method of claim 1 wherein the semivolatile species are stripped from said vapor fraction by contacting said vapor fraction with a mass transfer medium.

14. The method of claim 13 wherein the mass transfer medium comprises a solvent selected from the group consisting of benzyl alcohol, propylene carbonate, and gamma butyrolactone.

15. The method of claim 13 wherein the solvent is benzyl alcohol and the mass transfer medium comprises benzyl alcohol.

16. A method of recovering an aromatic alcohol solvent from an effluent comprising said aromatic alcohol solvent and less than 10 percent by weight of monomeric units, comprising the steps of
   (a) feeding the effluent to a heat exchanger type evaporator, and separating water and volatiles from the aromatic alcohol to provide a dewatered aromatic alcohol containing liquid;
   (b) evaporating the dewatered aromatic alcohol containing liquid in an evaporator to separate said aromatic alcohol from non-volatile materials and recovering therefrom
       (i) a vapor fraction comprising said aromatic alcohol; and
       (ii) a sludge fraction containing said nonvolatile materials and said aromatic alcohol; and
   (c) stripping semi-volatile species from said vapor fraction to provide a stripped vapor fraction comprising said aromatic alcohol and a liquid fraction comprising said semi-volatile species.

17. The method of claim 16 further comprising separating the vapor fraction in a fractionating unit into a higher vapor pressure fraction comprising a decomposition product of said aromatic alcohol and a lower vapor pressure fraction comprising said aromatic alcohol.

18. The method of claim 16 wherein the aromatic alcohol is benzyl alcohol.

19. The method of claim 17 wherein the aromatic alcohol is benzyl alcohol.

20. The method of claim 16 further comprising recovering the sludge fraction of step (b) and separating the sludge fraction to recover the aromatic alcohol therefrom.

21. The method of claim 20 wherein the sludge fraction is separated by feeding the sludge fraction to an evaporator to recover the aromatic alcohol therefrom and to provide a sludge waste.

22. The method of claim 21 wherein from about 5 ppm to about 500 ppm of a stabilizer is added to the waste sludge.

23. The method of claim 16 further comprising feeding the aromatic alcohol effluent to a filtering unit to remove particulate matter therefrom; wherein the aromatic alcohol effluent is fed to the filtering unit prior to step (a).

24. The method of claim 23 wherein the aromatic alcohol is benzyl alcohol.

* * * * *